Dec. 16, 1941. W. SCHAFER ET AL Plant Pat. 494
WALNUT TREE
Filed Nov. 18, 1940
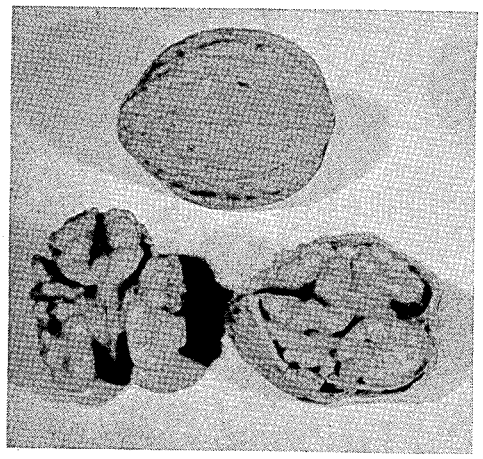
INVENTORS
Wilhelm Schafer
Marie Schafer Patented Dec. 16, 1941

Plant Pat. 494

UNITED STATES PATENT OFFICE

494

WALNUT TREE

Wilhelm Schafer and Marie Schafer, Yakima, Wash., assignors to H. Lynn Tuttle, Clarkston, Wash.

Application November 18, 1940, Serial No. 366,140

1 Claim. (Cl. 47—62)

This walnut tree was grown from seed brought to this country during the year 1920 from the Carpathian Mountain area of the Province of Bukowina in Europe, latitude 48 degrees, longitude 26 degrees east, a region of extreme, severe and changeable climate with temperatures to 50 degrees below zero. This particular tree is approximately twenty years from seed and altho moved several times has stood on our farm 2 miles west of Yakima for 15 years more or less. It is growing in a frosty location but bears good annual crops. It has attained a production of 270 pounds of nuts in one year. It has withstood, without injury, severe early winter freezes that have killed all other Persian Walnut (*Juglans regia*) known to have been growing anywhere in the district with the except of trees of this same stock. The nuts of this tree are large, full-meated and of very fine quality. The tree starts early in the spring, makes a rapid growth and matures its fruit early in the fall. The growing season required is short. Wood and buds harden early in the fall, their maturity season being about the same as with the American black walnut (*Juglans nigra*). The variety produces abundant pollen and bloom and is self-fertile. The detailed description below follows in general outlines used by the University of California in describing walnuts.

*Tree*

Rapid growing, vigorous, extremely hardy, large, spreading, head round. Branches rather light, tend to droop with crop. Leaves dark green, large, usually 9 leaflets but commonly varying from 5 to 9, rarely more. Average leaflet 6" long, 2½" wide but varying greatly in size and proportions, halves frequently of different size and shape, smooth edged, pointed, somewhat waved. Leaves may stay green until they fall. Bark green on new growth, grey-green to brownish green on older growth, smooth to very slight pubescence. Pith divisions vary from 40 or more to the inch to 1 to 5 or 6". Buds roundish ovate with very short, fine pubescence. Fruit almost round, dark green flecked with light green, usually single, in pairs or trios. Hull rather thin, may open either before or shortly after falling, in wet weather before. Nut of medium light brown, base rounding, wide parallel to suture, narrow at right angles to suture, apex has small point but otherwise depressed at suture, with high, prominent shoulders, good average size 1⅝" long, 1½" wide, 1⅜" thick, weight 10.8 grams. Individual nuts may show variation in shape from the typical. Shell webbed and lined with light, shallow grooves running irregularly lengthwise, somewhat pitted near suture, relatively smooth, very thin but dense and tough. The shell cracks more readily crosswise to the suture at the apex than along the suture. Suture prominent, tightly sealed and seldom opens when cracking. Inner surface of shell has definite flanges of thin membrane, otherwise smooth. Membrane between halves is relatively pronounced. Kernel rather square at apex but rounding to an ovate base, good average size 1⅜ x 1¼ x 1", weight 6.0 grams, very plump and full, averaging over 55% of the weight of the nut. Skin light brown to cream in color, showing some variation. Flavor and quality good, oily and rich. This nut is suitable for all domestic and commercial purposes. The variety is of important commercial value because: its hardy nature and early maturity of nuts, wood and buds permit it to be grown over a wide scope of country in the more northern latitudes of United States and at considerable elevations; it bears early, abundantly and regularly; the tightly joined halves of the nut tend to keep out dirt, worms and insects both before and after ripening; the very high percentage of meat also enhances commercial value.

We claim:

A new and distinct variety of Persian walnut, as herein described, characterized particularly by exceptional hardiness and productivity, adaptation to districts of short growing season, the tightness with which the two halves of the nut adhere together and the very high percentage of meat.

WILHELM SCHAFER.
MARIE SCHAFER.